(12) United States Patent
Eckman (10) Patent No.: US 8,206,292 B2
(45) Date of Patent: *Jun. 26, 2012

(54) WORKING CHANNEL FOR MINIMALLY INVASIVE SPINE SURGERY

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 283 days.

This patent is subject to a terminal disclaimer.

(21) Appl. No.: 12/632,137

(22) Filed: Dec. 7, 2009

(65) Prior Publication Data

US 2010/0081884 A1 Apr. 1, 2010

Related U.S. Application Data

(63) Continuation of application No. 11/258,800, filed on Oct. 26, 2005, now Pat. No. 7,651,499.

(60) Provisional application No. 60/622,262, filed on Oct. 26, 2004.

(51) Int. Cl.
 A61B 1/32 (2006.01)
 A61B 17/56 (2006.01)

(52) U.S. Cl. ...................................... 600/205; 606/86 A (58) Field of Classification Search .................. 600/205, 600/224, 215, 210, 157, 204, 218, 225, 231, 600/232, 233, 222; 606/86 A, 328, 266, 606/270, 198, 86 R
See application file for complete search history.

(56) References Cited

U.S. PATENT DOCUMENTS

| 3,624,800 | A | 11/1971 | Swick |
|---|---|---|---|
| 4,959,058 | A | 9/1990 | Michelson |
| 4,973,321 | A | 11/1990 | Michelson |
| 5,015,247 | A | 5/1991 | Michelson |
| 5,171,279 | A | 12/1992 | Mathews |
| 5,423,825 | A | 6/1995 | Levine |
| 5,437,683 | A | 8/1995 | Neumann et al. |
| 5,484,437 | A | 1/1996 | Michelson |
| D374,287 | S | 10/1996 | Goble et al. |
| 5,643,320 | A | 7/1997 | Lower et al. |
| 5,772,661 | A | 6/1998 | Michelson |
| 5,976,146 | A | 11/1999 | Ogawa et al. |
| 6,048,339 | A | 4/2000 | Zirps et al. |
| 6,053,907 | A | 4/2000 | Zirps |

(Continued)

FOREIGN PATENT DOCUMENTS

WO 2004021899 A1 3/2004

(Continued)

*Primary Examiner* — Pedro Philogene (74) *Attorney, Agent, or Firm* — Panitch Schwarze Belisario & Nadel LLP (57) ABSTRACT

A working channel for separating paraspinal muscles and minimizing muscle trauma during spinal surgery includes a flared upper section having a distal end, a proximal end and an interior lumen traversing through the flared upper section. The proximal end of the flared upper section having a larger cross-sectional area than the distal end of the flared upper section. A lower elongate body section extends fixedly from the distal end of the flared upper section. The lower elongate body section has a distal end for inserting into a patient, a proximal end connected to the flared upper section and an interior lumen traversing through the lower section. The flared upper section and the lower elongate body section each have an inner surface and an outer surface. A thickness between the inner and outer surfaces of the lower elongate body section is the same at each point along the longitudinal axis.

12 Claims, 6 Drawing Sheets

U.S. PATENT DOCUMENTS

| | | | |
|---|---|---|---|
| 6,080,155 | A | 6/2000 | Michelson |
| 6,083,228 | A | 7/2000 | Michelson |
| 6,159,179 | A | 12/2000 | Simonson |
| 6,159,214 | A | 12/2000 | Michelson |
| 6,187,000 | B1 | 2/2001 | Davison et al. |
| 6,241,734 | B1 | 6/2001 | Scribner et al. |
| 6,283,973 | B1 | 9/2001 | Hubbard et al. |
| 6,361,488 | B1 | 3/2002 | Davison et al. |
| 6,508,821 | B1 | 1/2003 | Schwartz et al. |
| 6,520,907 | B1 | 2/2003 | Foley et al. |
| 6,524,320 | B2 * | 2/2003 | DiPoto ............ 606/108 |
| 6,530,880 | B2 | 3/2003 | Pagliuca |
| 6,530,926 | B1 | 3/2003 | Davison |
| 6,547,795 | B2 | 4/2003 | Schneiderman |
| 6,554,836 | B2 | 4/2003 | Michelson |
| 6,652,553 | B2 | 11/2003 | Davison et al. |
| 6,692,501 | B2 | 2/2004 | Michelson |
| 6,702,741 | B2 * | 3/2004 | Rioux et al. ............ 600/233 |
| 6,800,084 | B2 * | 10/2004 | Davison et al. ........ 606/198 |
| 6,821,243 | B2 | 11/2004 | Pagliuca et al. |
| 6,896,680 | B2 | 5/2005 | Michelson |
| 6,916,330 | B2 | 7/2005 | Simonson |
| 6,929,606 | B2 | 8/2005 | Ritland |
| 6,951,538 | B2 | 10/2005 | Ritland |
| 6,986,772 | B2 | 1/2006 | Michelson |
| 7,008,431 | B2 | 3/2006 | Simonson |
| 7,033,362 | B2 | 4/2006 | McGahan et al. |
| 7,056,321 | B2 | 6/2006 | Pagliuca et al. |
| 7,074,226 | B2 | 7/2006 | Roehm, III et al. |
| 7,217,246 | B1 * | 5/2007 | Stone ................. 600/585 |
| 7,226,451 | B2 * | 6/2007 | Shluzas et al. ......... 606/86 R |
| 7,651,499 | B2 * | 1/2010 | Eckman ............. 606/86 R |
| 2002/0177897 | A1 | 11/2002 | Michelson |
| 2003/0032962 | A1 | 2/2003 | McGahan et al. |
| 2003/0083642 | A1 | 5/2003 | Boyd et al. |
| 2003/0083688 | A1 | 5/2003 | Simonson |
| 2003/0153927 | A1 | 8/2003 | DiPoto et al. |
| 2003/0199874 | A1 | 10/2003 | Michelson |
| 2004/0073213 | A1 | 4/2004 | Serhan et al. |
| 2004/0116954 | A1 | 6/2004 | Pagliuca et al. |
| 2004/0230100 | A1 | 11/2004 | Shluzas |
| 2004/0230309 | A1 | 11/2004 | DiMauro et al. |
| 2005/0070900 | A1 | 3/2005 | Serhan et al. |
| 2005/0075540 | A1 | 4/2005 | Shluzas et al. |
| 2005/0075644 | A1 | 4/2005 | DiPoto et al. |
| 2005/0080418 | A1 | 4/2005 | Simonson et al. |
| 2005/0090822 | A1 | 4/2005 | DiPoto |
| 2005/0090833 | A1 | 4/2005 | DiPoto |
| 2005/0090899 | A1 | 4/2005 | DiPoto |
| 2005/0107789 | A1 | 5/2005 | Sweeney |
| 2005/0131421 | A1 | 6/2005 | Anderson et al. |
| 2005/0137461 | A1 | 6/2005 | Marchek et al. |
| 2005/0154389 | A1 | 7/2005 | Selover et al. |
| 2005/0159650 | A1 | 7/2005 | Raymond et al. |
| 2005/0171551 | A1 | 8/2005 | Sukovich et al. |
| 2005/0192589 | A1 | 9/2005 | Raymond et al. |
| 2005/0215866 | A1 | 9/2005 | Kim |
| 2005/0245942 | A1 | 11/2005 | DiPoto |
| 2005/0251192 | A1 | 11/2005 | Shluzas et al. |
| 2005/0251196 | A1 | 11/2005 | Wong |
| 2005/0273131 | A1 | 12/2005 | Shluzas et al. |
| 2005/0273132 | A1 | 12/2005 | Shluzas et al. |
| 2005/0273133 | A1 | 12/2005 | Shluzas et al. |
| 2006/0030858 | A1 | 2/2006 | Simonson et al. |
| 2006/0030861 | A1 | 2/2006 | Simonson et al. |
| 2006/0069404 | A1 | 3/2006 | Shluzas et al. |
| 2006/0084981 | A1 | 4/2006 | Shluzas |
| 2006/0095039 | A1 | 5/2006 | Mutchler |

FOREIGN PATENT DOCUMENTS

| | | |
|---|---|---|
| WO | 2005084572 A2 | 9/2005 |
| WO | 2006052819 A2 | 5/2006 |
| WO | 2006058079 A2 | 6/2006 |

* cited by examiner

| Round Tubes | | | | |
|---|---|---|---|---|
| | 14 mm | 16 mm | 18 mm | 22 mm |
| Circumference ($2\pi r$) | 43.98 mm | 50.27 | 56.55 | 69.12 |
| Surface Area ($\pi r^2$) | 153.94 mm² | 201.06 | 254.47 | 380.13 |

| Parallelogram Working Channels | | |
|---|---|---|
| $L_x \times W_x$ | 22 x 18 | 24 x 20 |
| Perimeter Equivalent to Circumference (2 sides + 2 sides) | 58 mm | 62 mm |
| Surface Area Base x Altitude(height) | 210 mm² | 240 mm² |

WORKING CHANNEL FOR MINIMALLY INVASIVE SPINE SURGERY

CROSS REFERENCE TO RELATED APPLICATIONS

The present application is a continuation of U.S. patent application Ser. No. 11/258,800, filed on Oct. 26, 2005 and entitled "Working Channel for Minimally Invasive Spine Surgery," which claims priority to U.S. Provisional Patent Application No. 60/622,262 filed on Oct. 26, 2004, entitled "Working Channel for Minimally Invasive Spine Surgery."

BACKGROUND OF THE INVENTION

The present invention relates to an apparatus and method for performing spine surgery, and more particularly, to a working channel for minimally invasive spine surgery and a method for using the working channel.

Figure 1A:
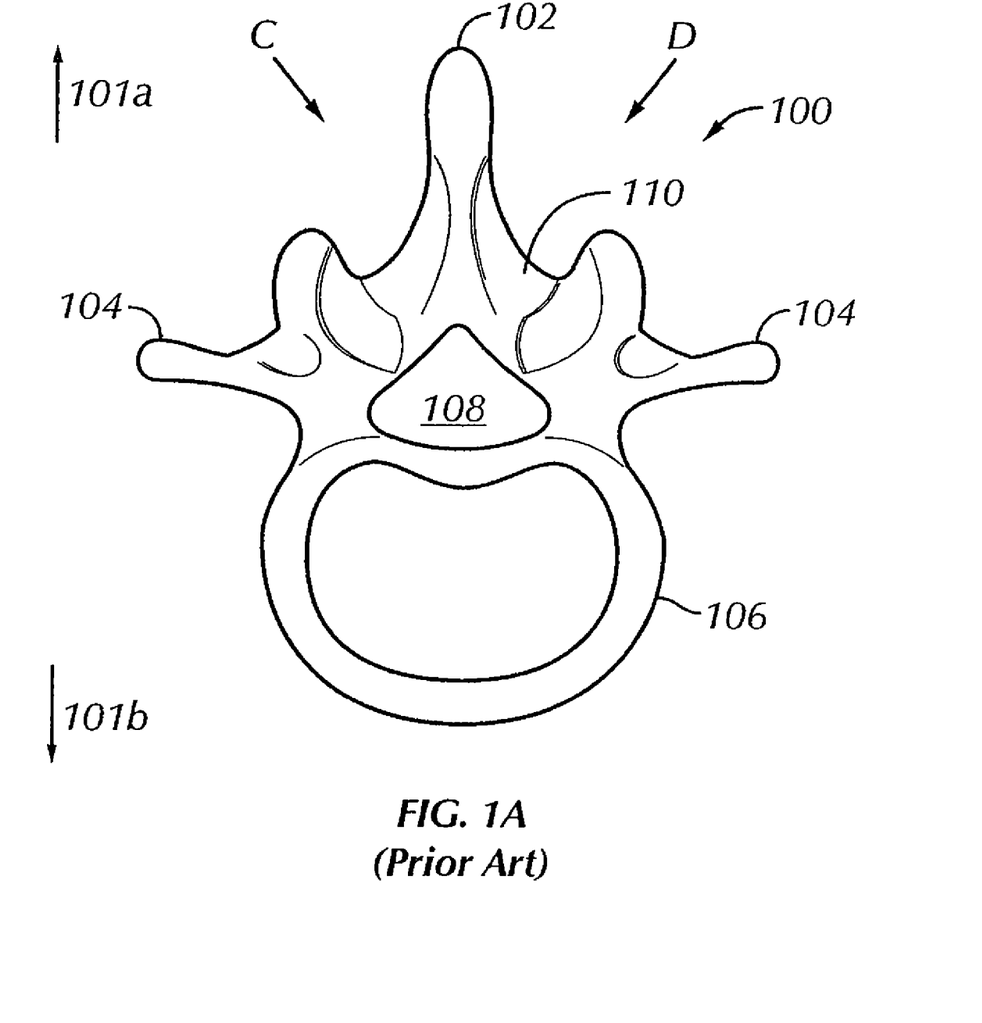
FIG. 1A is a top sectional view of a human vertebrae as is known in the art.
Figure 1B:
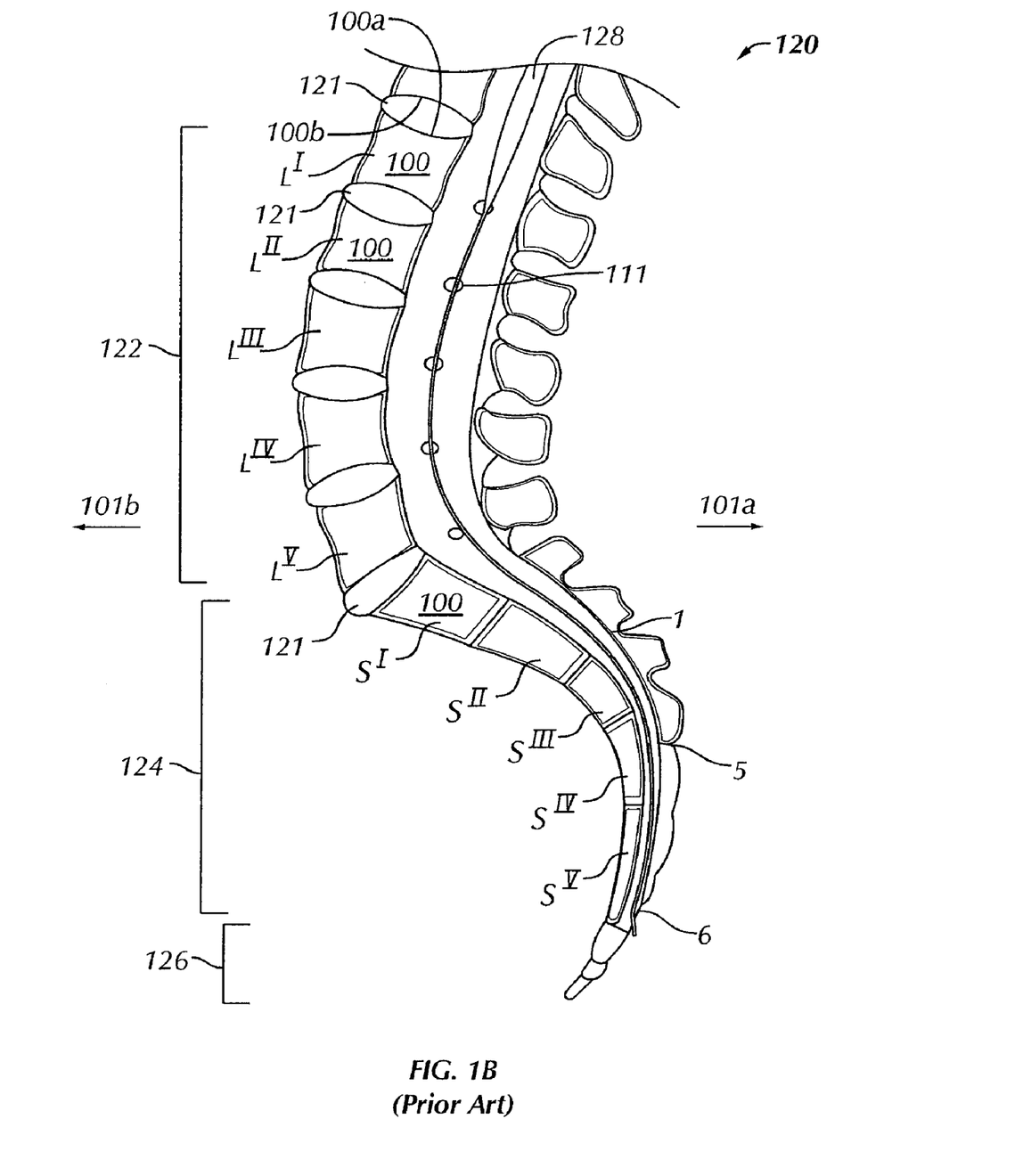
FIG. 1B is a side sectional view of the lumbar and sacral regions of a human spine as in known in the art.

Referring to prior art FIGS. 1A and 1B, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, or the like. The spine 120 includes seven cervical vertebrae (not shown), twelve thoracic vertebrae (not shown), five lumbar vertebrae, $L^1$-$L^V$, five sacral vertebrae, $S^1$-$S^V$, and three coccyx vertebrae 126. The sacral and coccyx vertebrae are each fused, thereby functioning as a single unit. FIG. 1B shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 1A, directional arrow 101a is pointing in the posterior direction and directional arrow 101b is pointing in the anterior direction. FIG. 1A shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 to reach their respective destinations within the body.

Recently, less invasive surgical techniques referred to as "minimally invasive" surgery have been developed to reduce the surgical trauma to a patient during spine surgery. In minimally invasive surgery, a much smaller incision is made than in normal open surgeries. A small retractor, working channel or tube is inserted through the posterior muscles (not shown) to allow access to the spine. Surgeons utilize special surgical instruments modified to work in such small openings such as curettes, osteotomes, reamers, probes, retractors, forceps or the like to access the spine while monitoring their technique using a microscope, fluoroscope (real-time X-ray monitoring), and/or an endoscope (a miniature TV camera with associated viewing monitor).

In order to access the area of interest in a minimally invasive spinal surgery, a working tube is installed through an incision in a patient's back. Presently available working tubes are typically round or ovoid. The round or ovoid shape places pressure on the skin in the area around an incision because the incisions are typically linear. Additionally, the round shape restricts access with surgical instruments between spinous processes and between pedicle and facet structures, thereby restricting possible movement of the instruments. Even further, the round shape makes moving the working tube along the sagittal plane difficult because of the large amount of surface area that is being pressed against muscle.

It is desirable to provide a working channel for minimally invasive spine surgery and a method for using such a working channel in order to allow access by a surgical instrument for performing minimally invasive spinal surgeries. The working channel should be easy to use, safe to insert into the body during surgery, provide for improved access and should not cause undesired damage to adjacent vertebrae. It is desirable to provide a minimally invasive surgical technique that allows for fast patient recovery times and that can be used on an outpatient basis.

BRIEF SUMMARY OF THE INVENTION

Briefly stated, the present invention is directed a working channel for separating paraspinal muscles and minimizing muscle trauma during spinal surgery. The working channel includes a flared upper section having a distal end, a proximal end and an interior lumen traversing through the flared upper section. The proximal end of the flared upper section having a larger cross-sectional area than the distal end of the flared upper section. A lower elongate body section extends fixedly from the distal end of the flared upper section. The lower elongate body section has a distal end which is the leading portion for inserting into a patient, a proximal end connected to the flared upper section and an interior lumen traversing through the lower section. The flared upper section and the lower elongate body section each have an inner surface and an outer surface. A thickness between the inner and outer surfaces of the lower elongate body section is the same at each point along the longitudinal axis.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the object described and designated parts thereof. The terminology includes the words above specifically mentioned, derivatives thereof and words of similar import. Additionally, the word "a", as used in the claims and in the corresponding portions of the specification, means "at least one."

Referring to the drawings in detail, wherein like reference numerals indicate like elements throughout, FIGS. 2-5 show a working channel 18 for spinal surgery in accordance with a first preferred embodiment of the present invention. The working channel 18 includes an elongate body 20 having a distal end 20a, a proximal end 20b and an interior lumen 20c traversing through the elongate body 20. The working channel 18 has an inner surface, which defines the interior lumen 20c, and an outer surface.

Figure 3:
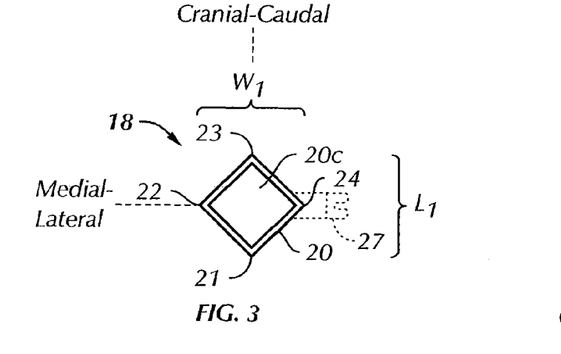
FIG. 3 is a top sectional view of a portion of the working channel of FIG. 2.

The elongate body 20 has a generally parallelogram-shaped cross-section (see FIG. 3). The parallelogram-shaped cross-section includes a first corner 21, a second corner 22, a third corner 23 and a fourth corner 24. The first and third corners 21, 23 are generally intended to point in the cranial and caudal directions of a patient, while the second and forth corners 22, 24 are generally intended to face the lateral and medial directions of a patient with respect to the posterior side of the patient. As shown in FIG. 3, the parallelogram-shaped cross-section includes four corners 21-24 that are generally pointed. Preferably, the cross-section of the interior lumen 20c defined by the elongate body 20 is similar to the cross-section of the outer periphery of the elongate body 20. Preferably, inner and outer cross-sections of the elongate body 20 taken along imaginary planes extending through the elongate body 20 and generally perpendicular to the walls of the elongate body 20 are dimensionally matched, meaning the relationship between the inner and outer cross-sections is the same at each point along a length of a longitudinal axis (not shown) extending from the distal end 20a to the proximal end 20b of the elongate body 20. Alternatively, a thickness between the inner and outer surface, as taken generally perpendicular to the longitudinal axis of the working channel, is the same at each point along the longitudinal axis. Preferably, walls of the elongate body 20 should be as thin as possible in order to maximize the access or working space available within the working channel 18.

The parallelogram-shaped outer cross-section of the elongate body 20 has a width $W_1$ as measured between the second and fourth corners 22, 24 and a sagittal length $L_1$ as measured between the first and third corners 21, 23. The width $W_1$ and sagittal length $L_1$ may be the same or different. The width $W_1$ may be greater than the sagittal length $L_1$ or the width $W_1$ may be less than the sagittal length $L_1$. Preferably, the width $W_1$ is slightly less than the sagittal length $L_1$. For example, the width $W_1$ may be about 18 mm and the sagittal length $L_1$ may be about 22 mm, or the width $W_1$ may be about 20 mm and the sagittal length $L_1$ may be about 24 mm.

The working channel 18 is preferably configured to be inserted through an incision less than about 50 mm in span. The working channel 18 may even be configured to be inserted through an incision less than about 25 mm in span or greater than about 50 mm in span. The elongate body 18 preferably is between about 5 mm and 30 mm in dimension as measured across cranial-caudal dimensions (sagittal length $L_1$) and the medial-lateral dimensions (width $W_1$), making it ideally suited for use in outpatient minimally invasive surgery.

In an alternate of the first preferred embodiment, a width $W_1$ and/or sagittal length $L_1$ of the proximal end 20b is greater than a width $W_1$ and/or sagittal length $L_1$ of the distal end 20a of the elongate body 20 (not clearly shown). The slope of the sidewalls may vary along the depth between the proximal end 20b and the distal end 20a in a linear or non-linear fashion creating other unique insertion mechanisms while improving exterior accessibility.

Figure 2:
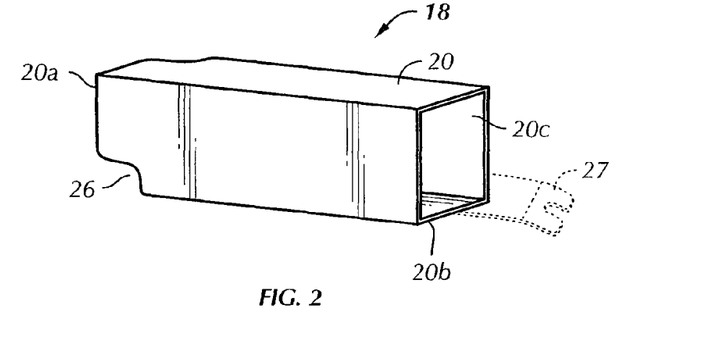
FIG. 2 is a perspective view of a working channel in accordance with a first preferred embodiment of the present invention.
Figure 4:
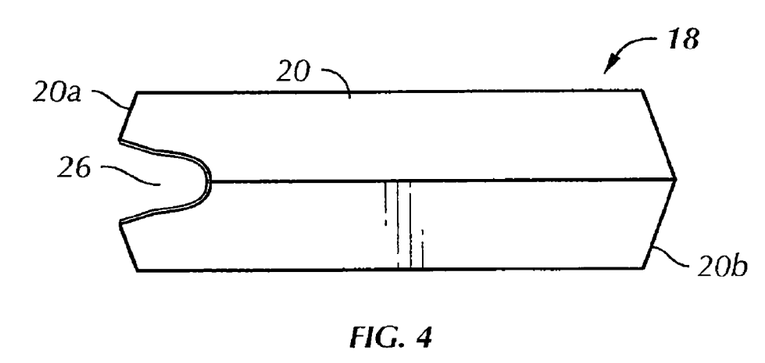
FIG. 4 is a cranial or caudal side elevational view of the working channel of FIG. 2.
Figure 5:
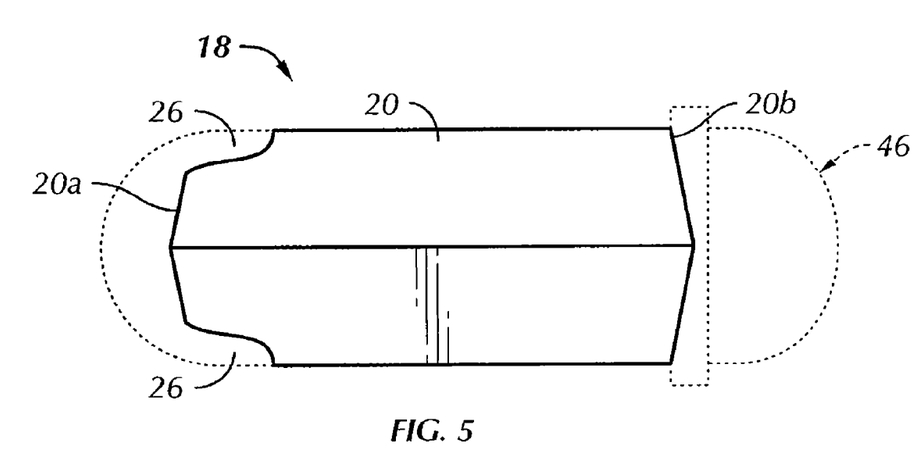
FIG. 5 is a medial or lateral side elevational view of the working channel of FIG. 2.

FIG. 4 is a cranial or caudal side elevational view of the working channel 18, and FIG. 5 is a medial or lateral side elevational view of the working channel of FIG. 2. As shown in FIGS. 2 and 4-5, the working channel 18 optionally includes slots 26 in the cranial-caudal sides.

Figure 6:
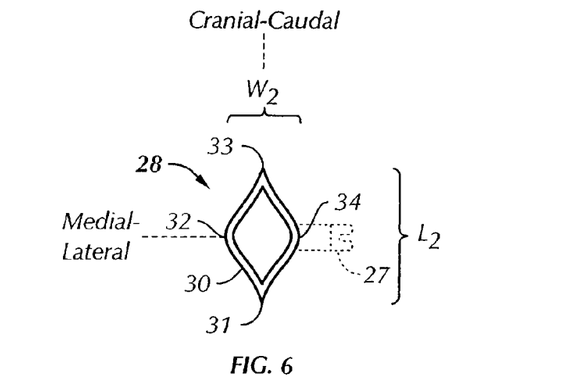
FIG. 6 is a top sectional view of a portion of a working channel in accordance with a second preferred embodiment of the present invention.

FIG. 6 is a top cross sectional view of a working channel 28 in accordance with a second preferred embodiment of the present invention. The outer cross-section of the working channel 28 of FIG. 6 is similar to the outer cross-section of the working channel 18 of FIG. 3 except that the medial and lateral sides are generally rounded. The working channel 28 has an elongate body 30 that has a generally parallelogram-shaped outer cross-section. The parallelogram-shaped outer cross-section has first, second, third and fourth corners 31, 32, 33, 34. The first and third corners 31, 33 are generally pointed and the second and forth corners 32, 34 are generally rounded. Thus, the second and forth corners 32, 34 each have a radius of curvature. Alternatively, the parallelogram-shaped outer cross-section may include four corners 31-34 that are generally rounded, and therefore, the four corners 31-34 would each have a radius of curvature. Preferably, the cross-section of the interior lumen 30c defined by the elongate body 30 is similar to the cross-section of the outer periphery of the elongate body 30. Preferably, walls of the elongate body 30 should be as thin as possible in order to maximize the access or working space available within the working channel 28.

The working channel 28 is preferably configured to be inserted through an incision less than about 50 mm in span. The working channel 28 may even be configured to be inserted through an incision less than about 25 mm in span or greater than about 50 mm in span. The elongate body 28 preferably is between about 5 mm and 30 mm in width $W_2$ and sagittal length $L_2$, making it ideally suited for use in outpatient minimally invasive surgery.

The parallelogram-shaped outer cross-section of the elongate body 30 has a width $W_2$ as measured between the second and fourth corners 32, 34 and a sagittal length $L_2$ as measured between the first and third corners 31, 33. The width $W_2$ and sagittal length $L_2$ may be the same or different. The width $W_2$ may be greater than the sagittal length $L_2$ or the width $W_2$ may be less than the sagittal length $L_2$. Preferably, the width $W_2$ is slightly less than the sagittal length $L_2$. For example, the width $W_2$ may be about 18 mm and the sagittal length $L_2$ may be about 22 mm, or the width $W_2$ may be about 20 mm and the sagittal length $L_2$ may be about 24 mm.

In an alternate of the second preferred embodiment, a width $W_2$ and/or sagittal length $L_2$ of the proximal end 20b is greater than a width $W_2$ and/or sagittal length $L_2$ of the distal end 20a of the elongate body 20 (not clearly shown). The slope of the sidewalls may vary along the depth in a linear or non-linear fashion creating other unique insertion mechanisms while improving exterior accessibility.

Figure 7:
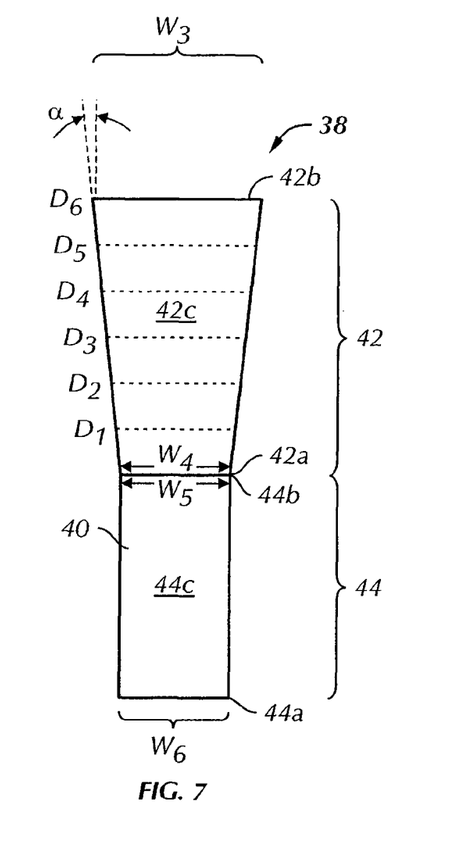
FIG. 7 is a side sectional view of a working channel in accordance with a third preferred embodiment of the present invention.

FIG. 7 is a side sectional view of a working channel 38 for spinal surgery in accordance with a third preferred embodiment of the present invention. The working channel 38 includes a flared upper section 42 having a distal end 42a, a proximal end 42b and an interior lumen 42c traversing through the flared upper section 42. The flared upper section 42 has an inner surface, which defines the interior lumen 42c, and an outer surface. The flared upper section 42 generally has a parallelogram-shaped outer cross-section similar to the first and/or second preferred embodiments. The flared upper section 42 may have other outer cross-section shapes such as ovoid, square, round, rectangular, polygonal or the like. The proximal end 42b of the flared upper section 42 has a width $W_3$ that is wider than a width $W_4$ of the distal end 42a of the flared upper section 42. Further, the proximal end 42b of the flared upper section 42 may have a larger cross-sectional area, as taken generally perpendicular to the longitudinal axis of the working channel, than the distal end 42a of the flared upper section 42. The flared upper section 42 slopes inwardly from the proximal end 42b toward the distal end 42a at an angle $\alpha$ with respect to a vertical axis. Preferably, the angle $\alpha$ is between about 3°-20° with respect to a vertical axis.

The flared upper section 42 may come in a variety of overall depths $D_1$-$D_6$ depending on the application. The depths $D_1$-$D_6$ may vary from may 1 to 6 centimeters (cm). The lower section 44 will be about 3-6 cm, but preferably the lower section 44 will be about 5 cm in depth. Thus, the overall working channel 38 can vary from 4-12 cm in depth.

The working channel 38 also includes a lower section 44 extending from the distal end 42a of the flared upper section 42. The lower section 44 has a distal end 44a, a proximal end 44b and an interior lumen 44c traversing through the lower section 44. The lower section has an inner surface, which defines the interior lumen 44c, and an outer surface. The lower section is going to be about 5 cm in depth. The lower section 44 generally has a parallelogram-shaped outer cross-section as well, similar to the first and second preferred embodiments. A width $W_5$ of the proximal end 44b of the lower section 44 is generally about the same as the width $W_4$ of the distal end 42a of the flared upper section 42. The lower section 44 preferably has a generally uniform width $W_5, W_6$ along the depth between the distal end 44a and the proximal end 44b of the lower section 44. However, the lower section 44 may also be slightly flared so that the width $W_5$ at the proximal end 44b is slightly greater or less than a width $W_6$ at the distal end 44a. Further, the slope of the flare as well as the cross-sectional shape of the lower section 44 may be different than that of the flared upper section 42, being similar in some ways to a two-stage funnel. Preferably, the cross-section of the interior lumen 44c defined by the lower section 44 is similar to the cross-section of the outer periphery of the lower section 44. Preferably, walls of the elongate body 40 should be as thin as possible in order to maximize the access or working space available within the working channel 38.

The flared upper section 42 and the lower section 44 are preferably formed as a one-piece elongate body 40. The one-piece elongate body 40 may be formed of molded or machined metal, alloys, polymeric material or the like.

The flared upper section 42 eases accessibility with long instruments, drills, endoscopes, suction tools, electrosurgical instruments or multiple instruments used in spine surgery. The reason for the flaring is that as the length of the elongate body 40 increases, the approach angle, angles of motion of instruments, the ability to perform dexterous tasks and visibility all diminish. Preferably, the flaring begins at an elevation that is beyond the muscle layer such as at the subcutaneous fat layer and skin or beyond. The flared upper section makes it much more feasible to conduct minimally invasive surgery for overweight patients.

The working channels 18, 28, 38 are preferably configured to be inserted through an incision between about 5 mm and about 100 mm in span, but is more preferably configured to be inserted through an incision of about 25-50 mm in span. Of course, the working channels 18, 28, 38 can be configured to be inserted through incisions or openings having other dimensions and can be used in conventional open surgery without departing from the present invention.

The portions of the working channels 18, 28, 38 intended to contact internal human body matter are formed of a biologically compatible material such as stainless steel, titanium, nickel plated metal, any biocompatible metal or alloy, a biocompatible ceramic, a biocompatible polymeric material or the like. Preferably, the working channels 18, 28, 38 are unitary structures that are molded or cast. The working channels 18, 28, 38 may also be formed of a clear polymeric material allowing for insulation from electrosurgical procedures such as cutting and/or coagulating and for increasing the field of view.

The working channels 18, 28, 38 also optionally include a slot 26 at the distal-most portion of the working channels 18, 28, 38 in the cranial-caudal sides for allowing more complex dexterous work to be performed in the confined area required by minimally invasive surgery such as screwing in pedicle screws, attaching fixation devices, tightening hardware or the like. This slot 26 could be applied to any shape working channel 18, 28, 38 or conventional working tube to improve the ability to move within the sagittal plane over pedicle screws and other attachment mechanisms extending out of vertebral bone.

The working channels 18, 28, 38 need not be a strict parallelogram-shaped cross-section, but rather, the "corners" 21-24, 31-34 where the side walls meet may be slightly or rounded or even chamfered.

Figure 8:
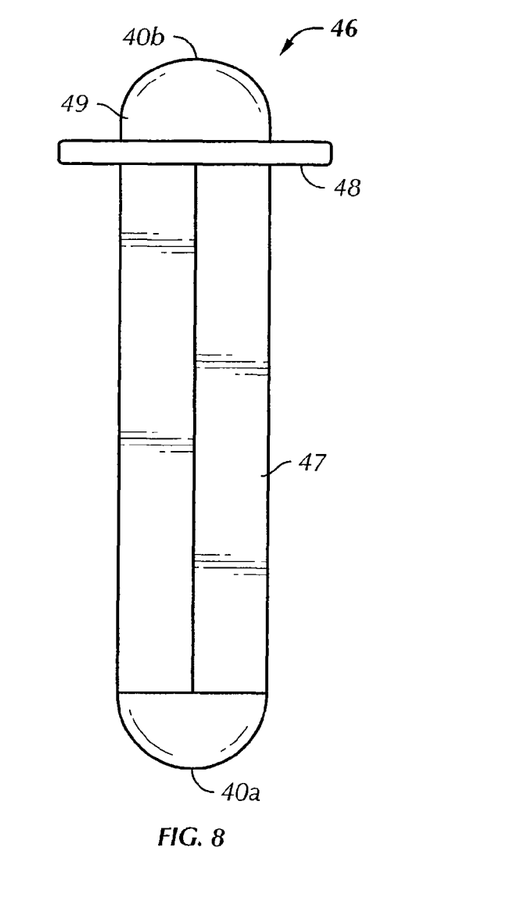
FIG. 8 is a side elevational view of an insertion tool for use with the preferred embodiments of the present invention.

FIG. 8 shows an insertion tool 46 for use with the preferred embodiments of the present invention. The insertion tool 46 has a distal end 46a and a proximal end 46b. The insertion tool 46 includes an elongate body 47 and a handle 49. Optionally, the insertion tool 46 can include a flange 48 to assist in pushing the working channel 18, 28, 38. The elongate body 47 is preferably shaped similar in cross-section to the respective working channel 18, 28, 38. The distal end of the working channel 18, 28, 38 may have a chamfered, radiused or ramped edge to blend with the elongate body 47 of the insertion tool 46. FIG. 5 shows the insertion tool 46 in phantom disposed inside the lumen 18c of the working channel 18 until the flange 48 engages the proximal end 20b of the working channel 18. The insertion tool 46 makes it easier to install the working channel 18, 28, 38 into an incision without the need to use time-consuming dilators (not shown) or the like. The insertion tool 46 may be formed of molded or machined metal, alloys, polymeric material or the like. However, the working channels 18, 28, 38 of the present invention can also be used with dilators.

Figure 10:
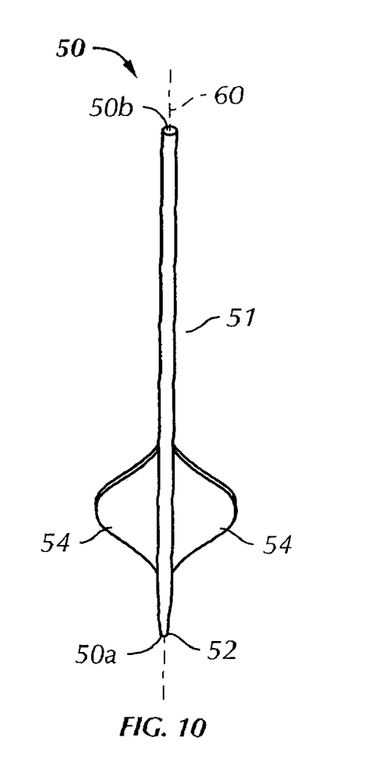
FIG. 10 is a side elevational view of a fascia knife for use in accessing the spine in minimally invasive procedures in accordance with the preferred embodiments of the present invention.
Figure 11:
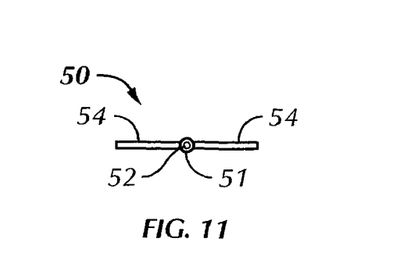
FIG. 11 is a top plan view of the fascia knife of FIG. 10.

FIGS. 10-11 show a fascia knife 50 for use in accessing the spine 120 in minimally invasive procedures in accordance with the preferred embodiments of the present invention. The fascia knife 50 has a distal end 50a and a proximal end 50b. The fascia knife 50 includes an elongate body 51 and an interior capillary 52. The interior capillary lumen 52 is configured to slidingly receive a surgical pin 60 (shown in phantom in FIG. 10), such as a Steinman pin. The interior capillary lumen 52 should preferably, but need not, extend entirely through the elongate body 51. The elongate body 51 has a diameter of about 2-5 mm and the blades 54 have a maximum span of about 5-25 mm. Preferably, the blades 54 are set-back about 2-2.5 cm from the distal end 50a of the fascia knife 50. Preferably, the blades 54 are sharpened in the distal direction and they reach their maximum span in 2-2.5 cm. Since the muscle is approximately 4-5 cm in depth, the blades 54 will need to begin cutting at an insertion depth of about 2-2.5 cm and need to complete cutting at an insertion depth of about 4-5 cm as measured from the distal end 52a of the fascia knife 50.

The working channel 18, 28, 38 is preferably used in outpatient spinal surgery. For example, in one method of using the working channel 18, 28, 38 in outpatient surgery, a surgeon makes an incision between about 10 mm and about 100 mm in span proximate a first vertebra 100 and a second vertebra 100 of a spine 129 of the patient. The incision is off-center with respect to the posterior-side of the spine 120 of the patient and is proximate to one of the laminae and the foramen 104 of the first and second vertebrae 100. A distal end 20a,44a of the working channel 18, 28, 38 is inserted into the incision to a desired depth proximate the first vertebra and the second vertebra 100 of the spine 120 accessible through the incision. The working channel 18, 28, 38 generally has a parallelogram-shaped outer cross-section. One of the first vertebra 100, the second vertebra 100 and a small gap between the first and second vertebrae 100 are accessed through the working channel 18, 28, 38. Optionally, before inserting the working channel 18, 28, 38, the surgeon may use a finger or a blunt surgical instrument (not shown) smaller than the working channel 18, 28, 38 to gently move apart fat, muscle, tendons or the like.

In another method of using a working channel 18, 28, 38 in outpatient spine surgery, a surgeon inserts a distal end of a surgical pin 60 in a posterior region of a patient proximate the small gap between the first vertebra 100 and the second vertebra 100 of the spine 120 accessible through the incision. The surgeon then makes an incision between about 10 mm and about 100 mm in span in a posterior region of a patient proximate a small gap between a first vertebra 100 and a second vertebra 100 of a spine 120 of the patient. The small gap is preferably off-center with respect to the posterior-side of the spine 120 of the patient and proximate to the laminae or a foramen 104 of the first and second vertebrae 100. The surgeon slips the fascia knife 50 over the surgical pin 60 such that the interior capillary lumen 52 of the fascia knife 50 receives the surgical pin 60. As the surgeon moves the fascia knife 50 distally, the blades 54 of the fascia knife 50 cut through fascia covering the paraspinal muscles providing easier access for the working channel 18, 28, 38. The surgeon then removes the fascia knife 50 and surgical pin 60. The surgeon inserts the combination of the working channel 18, 28, 38 and the insertion tool 46 to the desired depth and then removes the insertion tool 46 leaving the working channel 18, 28, 38 for accessing the spine 120. The surgeon can then slide the working channel 18, 28, 38 along the cranial and caudal directions.

In yet another method of using a working channel 18, 28, 38 in outpatient spine surgery, the surgeon can insert a distal end of a dilator (not shown) over the surgical pin 60 proximate the small gap between the first vertebra 100 and the second vertebra 100 of the spine 120 accessible through the incision. The surgeon may remove the surgical pin 60 at this time or later. More than likely, the surgeon will need to successively insert a plurality of increasingly larger dilators over the previous dilator proximate the small gap between the first vertebra 100 and the second vertebra 100 of the spine 120 accessible through the incision, in order to gently expand the area of interest. Preferably, each dilator generally has a parallelogram-shaped outer cross-section similar to the working channel 18, 28, 38. But, the dilator may be other shapes without departing from the invention. The surgeon inserts a distal end 20a,44a of the working channel 18, 28, 38 over the dilator proximate the small gap between the first vertebra 100 and the second vertebra 100 of the spine 120 accessible through the incision. The working channel 18, 28, 38 generally has a parallelogram-shaped outer cross-section, as mentioned above, thereby being eased over the dilator(s) which had previously expanded (dilated) the fascia and muscle in the area of interest. The surgeon removes the dilator(s) and the surgical pin 60 through the working channel 18, 28, 38. The working channel 18, 28, 38 permits the surgeon to access one of the first vertebra 100, the second vertebra 100 and a small gap between the first vertebra 100 and the second vertebra 100 of the spine 120 for performing a surgical procedure or investigation.

Figure 9:
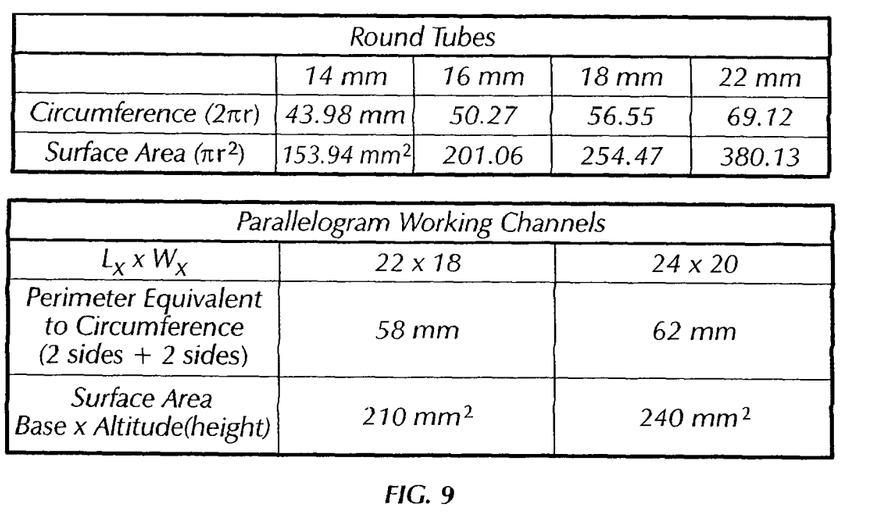
FIG. 9 is a table comparing the circumference and surface area of a conventional round working tube to the perimeter measurement and surface area of a working channel in accordance with the preferred embodiments of the present invention.

Because a parallelogram-shaped outer cross-section working channel 18, 28, 38 has a smaller perimeter, there is less pressure on skin edges as compared to conventional round or ovoid working tubes. Because a parallelogram-shaped outer cross-section working channel 18, 28, 38 has a smaller surface area, it allows less muscle displacement as compared to conventional round or ovoid working tubes, and therefore, results in less bleeding and pain once the working channel 18, 28, 38 is removed. FIG. 9 is a comparison of the perimeter (circumference) and surface area of a conventional round working tube to the perimeter measurement and surface area of a working channel 18 in accordance with the preferred embodiments of the present invention. Obviously, the working channel 28 has a non-geometric shape whose surface area would require much more complicated area calculations using software; however the parallelogram-shape can roughly approximate its surface area.

Additionally, the parallelogram-shaped outer cross-section of the working channel 18, 38 provides less resistance when performing sliding movements along or parallel to the sagittal plane or axis. The working channel 28 of the second preferred embodiment has a parallelogram-shaped outer cross-section (FIG. 4) with at least two rounded corners 32, 34, and the rounded corners 32, 34 (inserted at the medial and lateral sides) provide even less resistance when moving cranially-caudally within the incision (i.e., like a boat keel cutting through water). The muscle and tissue are gently pushed apart by the parallelogram-shaped outer cross-section instead of being bluntly shoved by a conventional round tube which typically results in muscle tearing or having to be cut or (undesirably) "popping" under the round working channel right into the "field of vision."

Optionally, the working channel 18, 28, 38 includes a handle or clamping attachment or other fixing mechanism 27 (shown in phantom in FIGS. 2-4) for securing the working channel 18, 28, 38 at a particular elevation and/or angle relative to the patient. Such handle 27 may work with an extensible, bendable clamping bracket or with a rigid frame or vise (not shown) as is known in the art.

From the foregoing, it can be seen that the present invention is directed to a working channel for minimally invasive spine surgery and methods for using the same. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A working channel for separating paraspinal muscles and minimizing muscle trauma during spinal surgery comprising:
    a flared upper section having a distal end, a proximal end and an interior lumen traversing through the flared upper section, the proximal end of the flared upper section having a larger cross-sectional area, as taken generally perpendicular to a longitudinal axis of the working channel, than the distal end of the flared upper section; and
    a lower elongate body section extending fixedly from the distal end of the flared upper section, the lower elongate body section being rigid and having a distal end which is the leading portion for inserting into a patient, a proximal end connected to the flared upper section and an interior lumen traversing through the lower section,
    wherein the flared upper section and the lower elongate body section each have an inner surface and an outer surface, and wherein a thickness between the inner and outer surfaces of the lower elongate body section, as taken generally perpendicular to the longitudinal axis of the working channel, is the same at each point along the longitudinal axis.

2. The working channel of claim 1, wherein a cross-section of the lower elongate body section generally is marquise-shaped.

3. The working channel of claim 1, wherein a cross-sectional area, as taken generally perpendicular to the longitudinal axis of the working channel, of the inner and outer surfaces of the lower elongate body section is generally uniform in size and shape between the distal end and the proximal end thereof.

4. The working channel of claim 1, wherein a cross-sectional area, as taken generally perpendicular to a longitudinal axis of the working channel, of the inner and outer surfaces at the proximal end of the lower elongate body section is larger than a cross-sectional area, as taken generally perpendicular to a longitudinal axis of the working channel, of the inner and outer cross-sections of the distal end of the lower elongate body section.

5. The working channel of claim 1, wherein a cross-section of the flared upper section generally is marquise-shaped.

6. The working channel of claim 1, wherein the lower elongate body section of the working channel includes a slot at the distal end.

7. The working channel of claim 1, further comprising only a single lumen that extends therethrough.

8. The working channel of claim 1, further comprising a fixing mechanism for fixing the working channel at a particular elevation and/or angle relative to a patient.

9. The working channel of claim 1, wherein the flared upper section slopes inwardly from the proximal end toward the distal end at an angle between about 3°-20° with respect to the longitudinal axis.

10. The working channel of claim 1, wherein the flaring of the flared upper section is at an elevation that is outward of a muscle layer of a patient.

11. The working channel of claim 1, wherein the flared upper section and the lower elongate body section are formed as a one-piece elongate body.

12. The working channel of claim 1, wherein the flared upper section is rigid.

* * * * *